US009498147B2

United States Patent
Massarwa et al.

(10) Patent No.: US 9,498,147 B2
(45) Date of Patent: Nov. 22, 2016

(54) ENHANCED ECG CHART PRESENTATION

(71) Applicant: BIOSENSE WEBSTER (ISRAEL) LTD., Yokneam (IL)

(72) Inventors: Fady Massarwa, Baka El Gharbiya (IL); Akram Zoabi, Kfar Masser (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 122 days.

(21) Appl. No.: 14/168,291

(22) Filed: Jan. 30, 2014

(65) Prior Publication Data

US 2015/0208935 A1 Jul. 30, 2015

(51) Int. Cl.
| | |
|---|---|
| *A61B 5/044* | (2006.01) |
| *A61B 5/0205* | (2006.01) |
| *A61B 5/00* | (2006.01) |
| *A61B 5/0432* | (2006.01) |
| *A61B 5/06* | (2006.01) |
| *A61B 5/0408* | (2006.01) |
| *A61B 5/0452* | (2006.01) |
| *A61B 18/14* | (2006.01) |
| *A61B 18/00* | (2006.01) |
| *A61B 5/053* | (2006.01) |
| *A61B 5/01* | (2006.01) |
| *A61B 5/05* | (2006.01) |

(52) U.S. Cl.
CPC ........... *A61B 5/044* (2013.01); *A61B 5/02055* (2013.01); *A61B 5/0432* (2013.01); *A61B 5/0452* (2013.01); *A61B 5/04085* (2013.01); *A61B 5/062* (2013.01); *A61B 5/6852* (2013.01); *A61B 5/6885* (2013.01); *A61B 5/7221* (2013.01); *A61B 5/7435* (2013.01); *A61B 18/1492* (2013.01); *A61B 5/01* (2013.01); *A61B 5/05* (2013.01); *A61B 5/0538* (2013.01); *A61B 5/06* (2013.01); *A61B 5/6823* (2013.01); *A61B 5/6869* (2013.01); *A61B 2018/00357* (2013.01); *A61B 2018/00577* (2013.01); *A61B 2034/2051* (2016.02); *A61B 2034/2063* (2016.02); *A61B 2090/065* (2016.02); *A61B 2218/002* (2013.01); *A61B 2562/0223* (2013.01)

(58) Field of Classification Search
None
See application file for complete search history.

(56) References Cited

U.S. PATENT DOCUMENTS

| | | | |
|---|---|---|---|
| 5,391,199 | A | 2/1995 | Ben-Haim |
| 5,443,489 | A | 8/1995 | Ben-Haim |
| 5,558,091 | A | 9/1996 | Acker |
| 5,803,084 | A | 9/1998 | Olson |

(Continued)

FOREIGN PATENT DOCUMENTS

| | | |
|---|---|---|
| EP | 2057942 A1 | 5/2009 |
| WO | WO 2007/015139 A2 | 2/2007 |

(Continued)

OTHER PUBLICATIONS

European Search Report dated Jun. 22, 2015 for corresponding Application No. EP15153012.

*Primary Examiner* — Erica Lee

(57) ABSTRACT

A method, including collecting first data samples of electrical potentials produced by a heart at a sequence of sampling times, and collecting second data samples of ancillary data with respect to the heart at the sampling times. Based on the first and second data samples, a trace of the electrical potentials collected at the sampling times is presented, on a display, the trace having a pseudo-three-dimensional (3D) characteristic that varies responsively to the ancillary data collected at each of the sampling times.

13 Claims, 3 Drawing Sheets

(56) References Cited

U.S. PATENT DOCUMENTS

| | | |
|---|---|---|
| 5,944,022 A | 8/1999 | Nardella |
| 5,983,126 A | 11/1999 | Wittkampf |
| 6,172,499 B1 | 1/2001 | Ashe |
| 6,177,792 B1 | 1/2001 | Govari |
| 6,456,864 B1 | 9/2002 | Swanson |
| 6,471,693 B1 | 10/2002 | Carroll et al. |
| 6,690,963 B2 | 2/2004 | Ben-Haim |
| 6,788,967 B2 | 9/2004 | Ben-Haim |
| 2003/0028119 A1 | 2/2003 | Xue et al. |
| 2004/0111021 A1 | 6/2004 | Olson |
| 2006/0258947 A1 | 11/2006 | Olson |
| 2008/0058656 A1* | 3/2008 | Costello et al. ............ 600/508 |
| 2009/0093806 A1 | 4/2009 | Govari |
| 2009/0138007 A1 | 5/2009 | Govari |
| 2013/0109988 A1* | 5/2013 | Kim et al. ................ 600/515 |
| 2013/0190637 A1 | 7/2013 | Zhang |
| 2014/0125477 A1* | 5/2014 | Kasuya et al. ............. 340/525 |

FOREIGN PATENT DOCUMENTS

| | | |
|---|---|---|
| WO | WO 2008/008796 A2 | 1/2008 |
| WO | WO 2008/135731 A1 | 11/2008 |

* cited by examiner

ENHANCED ECG CHART PRESENTATION

FIELD OF THE INVENTION

The present invention relates generally to electrocardiography (ECG), and specifically to a system that presents ECG and ancillary electrophysiological data in a single chart.

BACKGROUND OF THE INVENTION

During a medical procedure such as cardiac ablation, there are typically simultaneous streams of real-time data that an operator (e.g., a physician) monitors while performing the procedure. For example, while using an intracardiac catheter to perform an ablation on intracardiac tissue, the operator may want to keep track of real-time electrophysiological (EP) data such as electrocardiography (ECG) data, and ancillary data such as locations of the catheter's distal tip and ablation energy being delivered to the heart tissue.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY OF THE INVENTION

There is provided, in accordance with an embodiment of the present invention a method, including collecting first data samples of electrical potentials produced by a heart at a sequence of sampling times, collecting second data samples of ancillary data with respect to the heart at the sampling times, and presenting, on a display, based on the first and second data samples, a trace of the electrical potentials collected at the sampling times, the trace having a pseudo-three-dimensional (3D) characteristic that varies responsively to the ancillary data collected at each of the sampling times.

In some embodiments, the first data samples include electrical impulses conveyed from body surface electrodes, and the ancillary data includes measurements collected from one or more sensors contained within a distal end of a flexible insertion tube configured for insertion into a heart. In additional embodiments, the measurements can be selected from a list consisting of ablation energy, a location of a distal end of the catheter, a measurement of a force exerted by the distal end on endocardial tissue of the heart, a quality of contact between the distal end and the endocardial tissue, a magnitude and a phase of impedance detected by the body surface electrodes, a temperature of the endocardial tissue, a Force Power Time Integral, and irrigation fluid parameters.

In some embodiments, presenting the trace having the pseudo-3D characteristic includes presenting, on the display, a ribbon chart having a ribbon including first and second lines, the second line following a contour of the first line. In additional embodiments, the pseudo-3D characteristics can be selected from a list consisting of third lines connecting the first and the second lines, a shading of one or more regions between the first and the second lines, a thickness of the ribbon, shading the thickness of the ribbon, and a color of the ribbon. In further embodiments, the ribbon chart has multiple axes including a vertical axis, a horizontal axis and a pseudo-depth axis, and the method includes presenting a rotation of the ribbon chart along one of the axes.

In supplementary embodiments, the method includes presenting an icon on the ribbon chart indicating an occurrence of one or more events, and presenting information on the one or more events upon receiving an input selecting the icon. In additional embodiments, the method includes saving the first and the second data samples to a memory.

There is also provided, in accordance with an embodiment of the present invention apparatus, including a display, and a processor configured to collect first data samples of electrical potentials produced by a heart of a patient at a sequence of sampling times, to collect second data samples of ancillary data with respect to the heart at the sampling times, and to present, on the display, based on the first and second data samples, a trace of the electrical potentials collected at the sampling times, the trace having a pseudo-three-dimensional (3D) characteristic that varies responsively to the ancillary data collected at each of the sampling times.

There is further provided, in accordance with an embodiment of the present invention a computer software product, the product including a non-transitory computer-readable medium, in which program instructions are stored, which instructions, when read by a computer, cause the computer to collect first data samples of electrical potentials produced by a heart at a sequence of sampling times, to collect second data samples of ancillary data with respect to the heart at the sampling times, and to present, on a display, based on the first and second data samples, a trace of the electrical potentials collected at the sampling times, the trace having a pseudo-three-dimensional (3D) characteristic that varies responsively to the ancillary data collected at each of the sampling times.

BRIEF DESCRIPTION OF THE DRAWINGS

The disclosure is herein described, by way of example only, with reference to the accompanying drawings, wherein.

DETAILED DESCRIPTION OF EMBODIMENTS

Overview

Embodiments of the present invention provide methods and systems for presenting ECG and ancillary data as a single chart on a display. During a medical procedure such as cardiac tissue, the ancillary data may comprise measurements received from a distal end of an intracardiac catheter within a cardiac chamber, such as a temperature of intracardiac tissue, positions of the distal end, and a measurement of ablation energy delivered by the distal end to the intracardiac tissue.

In some embodiments, the ECG data can be presented as a chart (e.g., a line chart) on the display, and the ancillary data can be presented as a pseudo-three-dimensional (3D) enhancement of the chart. By combining ECG and ancillary data into a single chart, embodiments of the present invention enable an operator to track multiple ECG and ancillary data parameters by looking at a single chart.

As described hereinbelow, upon collecting first data samples of electrical potentials produced by a heart at a sequence of sampling times, the first data samples are presented as an ECG chart on a display, the ECG chart comprising a trace of the electrical potentials collected at the sampling times. In addition to collecting the first data, second data samples of ancillary data with respect to the heart are also collected at the sampling times, and the second data is presented as a pseudo-three-dimensional trace that varies responsively to the ancillary data collected at each of the sampling times.

System Description

Figure 1:
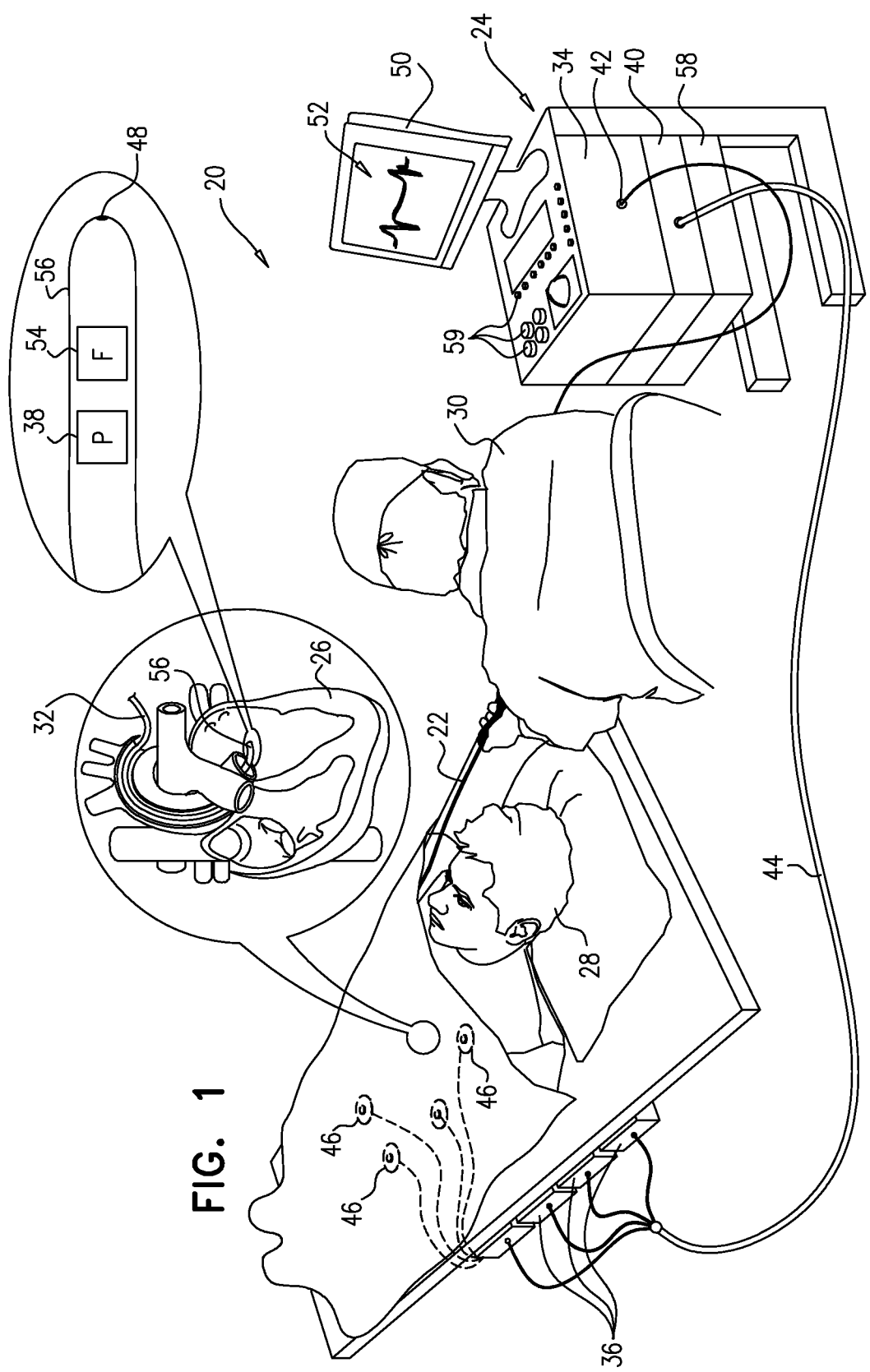
FIG. 1 is a schematic, pictorial illustration of a medical system configured to present an enhanced electrocardiography (ECG) chart, in accordance with an embodiment of the present invention.

FIG. 1 is a schematic, pictorial illustration of a medical system 20 configured to present an enhanced ECG chart 52, in accordance with an embodiment of the present invention. System 20 comprises a probe 22, such as an intracardiac catheter, and a control console 24. In embodiments described hereinbelow, it is assumed that probe 22 is used for diagnostic or therapeutic treatment, such as for mapping electrical potentials in a heart 26 of a patient 28. Alternatively, probe 22 may be used, mutatis mutandis, for other therapeutic and/or diagnostic purposes in the heart or in other body organs.

An operator 30 inserts probe 22 through the vascular system of patient 28 so that a distal end 32 of probe 22 enters a chamber of heart 26. Console 24 typically uses magnetic position sensing to determine position coordinates of distal end inside heart 26. To determine the position coordinates, a driver circuit 34 in console 24 drives field generators 36 to generate magnetic fields within the body of patient 28. Typically, field generators 36 comprise coils, which are placed below the patient's torso at known positions external to patient 28. These coils generate magnetic fields in a predefined working volume that contains heart 26.

A magnetic field sensor 38 (also referred to herein as location sensor 38) within distal end 32 of probe 22 generates electrical signals in response to these magnetic fields. A signal processor 40 processes these signals in order to determine the position coordinates of distal end 32, typically including both location and orientation coordinates. The method of position sensing described hereinabove is implemented in the CARTO™ mapping system produced by Biosense Webster Inc., of Diamond Bar, Calif., and is described in detail in the patents and the patent applications cited herein.

Location sensor 38 transmits a signal to console 24 that is indicative of the location coordinates of distal end 32. Location sensor 38 may comprise one or more miniature coils, and typically comprises multiple coils oriented along different axes. Alternatively, location sensor 38 may comprise either another type of magnetic sensor, or position transducers of other types, such as impedance-based or ultrasonic location sensors. Although FIG. 1 shows a probe with a single location sensor, embodiments of the present invention may utilize probes with more than one location sensor.

Although in the present example system 20 measures the position of distal end 32 using magnetic-based sensors, other position tracking techniques may be used (e.g., impedance-based sensors). Magnetic position tracking techniques are described, for example, in U.S. Pat. Nos. 5,391,199, 5,443,489, 6,788,967, 6,690,963, 5,558,091, 6,172,499 6,177,792, whose disclosures are incorporated herein by reference. Impedance-based position tracking techniques are described, for example, in U.S. Pat. Nos. 5,983,126, 6,456,864 and 5,944,022, whose disclosures are incorporated herein by reference.

Processor 40 typically comprises a general-purpose computer, with suitable front end and interface circuits for receiving signals from probe 22 and controlling the other components of console 24. Processor 40 may be programmed in software to carry out the functions that are described herein. The software may be downloaded to console 24 in electronic form, over a network, for example, or it may be provided on non-transitory tangible media, such as optical, magnetic or electronic memory media. Alternatively, some or all of the functions of processor 40 may be carried out by dedicated or programmable digital hardware components.

In the example of FIG. 1, console 24 is also connected by a cable 44 to body surface electrodes, which typically comprise adhesive skin patches 46 attached to the patient's skin. In embodiments of the present invention, the surface electrodes can pick up electrical impulses generated by the polarization and depolarization of cardiac tissue, and convey the impulses to console 24 via cable 44.

An input/output (I/O) interface 42 enables console 24 to interact with probe 22 and the surface electrodes. Based on the electrical impulses received from the surface electrodes and signals received from probe 22 (via interface 42 and other components of system 20), processor 40 drives a display 50 to present operator 30 with chart 52 (also referred to herein as an enhanced ECG chart 52), as described in detail hereinbelow.

Probe 22 also comprises a force sensor 54 contained within distal end 32. Force sensor 54 measures a force applied by a distal tip 56 of probe 22 to the endocardial tissue of heart 26 by generating a signal to the console that is indicative of the force exerted by the distal tip on the endocardial tissue. In one embodiment, the force sensor may comprise a magnetic field transmitter and receiver connected by a spring in distal end 32, and may generate an indication of the force based on measuring the deflection of the spring. Further details of this sort of probe and force sensor are described in U.S. Patent Application Publications 2009/0093806 and 2009/0138007, whose disclosures are incorporated herein by reference. Alternatively, distal end 32 may comprise another type of force sensor.

In some embodiments, probe 22 may comprise an electrode 48 coupled to the distal end and configured to function as an impedance-based position transducer. Additionally or alternatively, electrode 48 can be configured to measure a certain physiological property (e.g., the local surface electrical potential) at each of the multiple locations. In further embodiments, electrode 48 can be used to ablate endocardial tissue in heart 26.

During the diagnostic treatment, processor 40 presents chart 52 and stores data representing the chart in a memory 58. Memory 58 may comprise any suitable volatile and/or non-volatile memory, such as random access memory or a hard disk drive. In some embodiments, operator 30 can manipulate chart 52 using one or more input devices 59.

Figure 2:
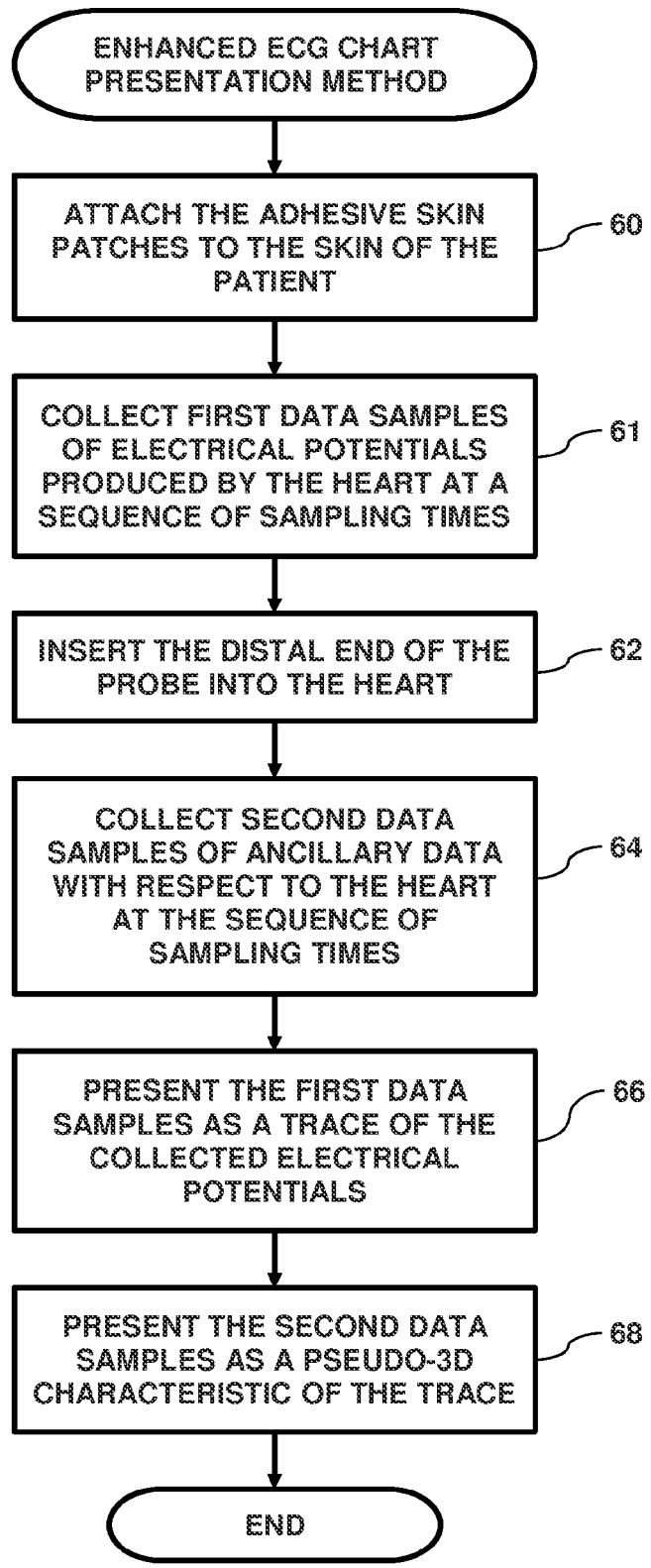
FIG. 2 is a flow diagram that schematically illustrates a method of presenting the ECG chart that includes ancillary data, in accordance with an embodiment of the present invention.
Figure 4:
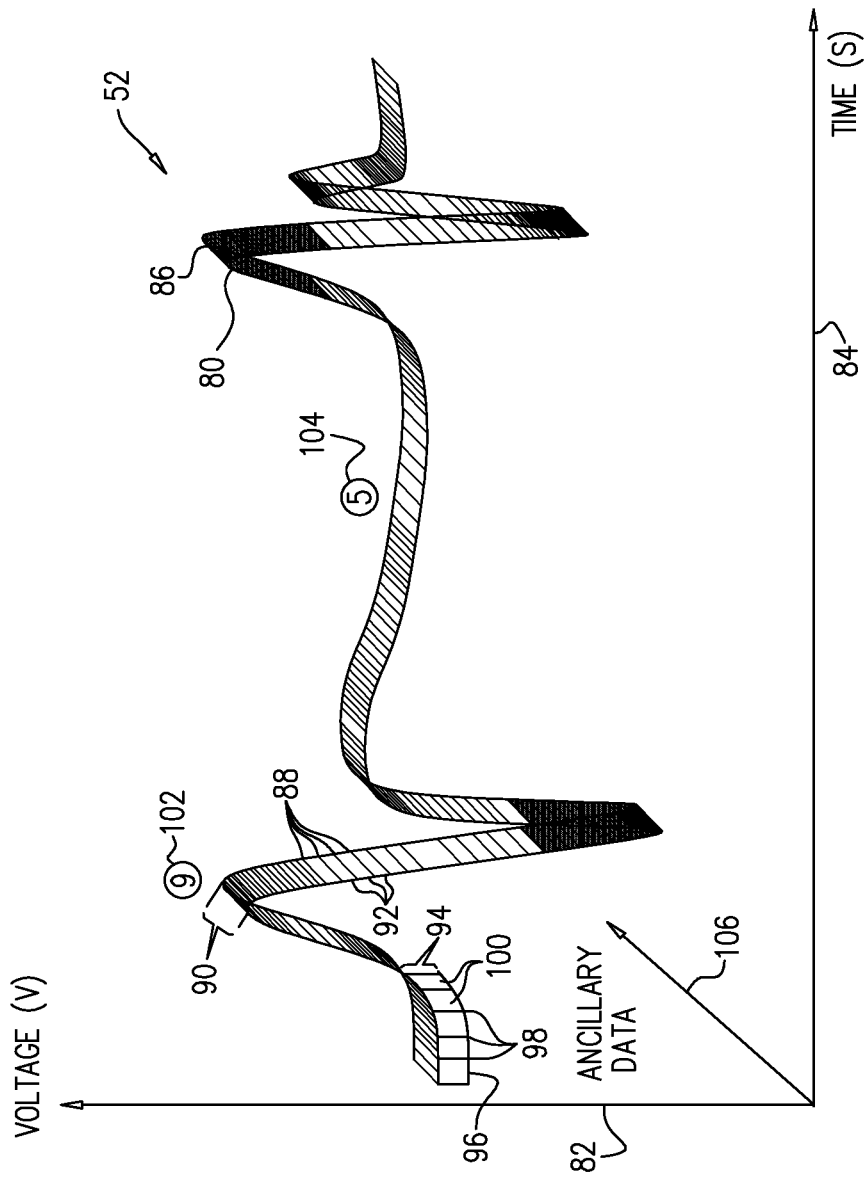
FIG. 4 is a schematic view of the enhanced chart showing ECG and ancillary data, in accordance with an embodiment of the present invention.
Figure 3:
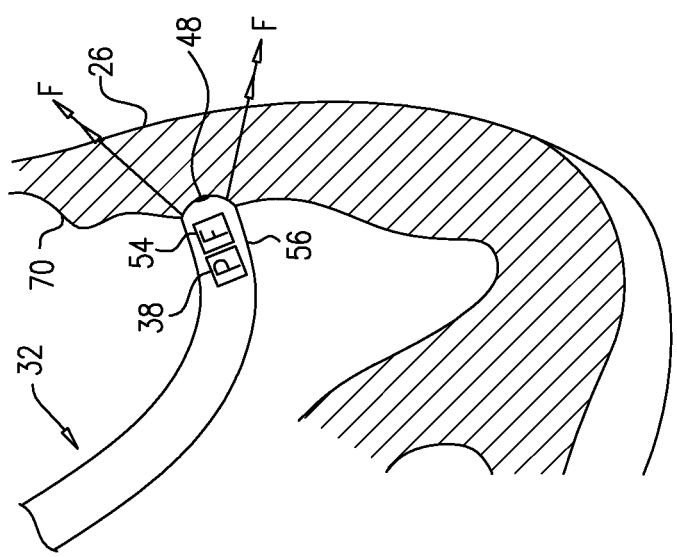
FIG. 3 is a schematic view showing a distal tip of a catheter in contact with endocardial tissue of a cardiac chamber, in accordance with an embodiment of the present invention.

FIG. 2 is a flow diagram that schematically illustrates a method of presenting chart 52 showing ECG and ancillary data collected during a procedure on heart 26, FIG. 3 is a schematic detail view showing distal tip 56 in contact with endocardial tissue 70 of the heart, and FIG. 4 is a schematic detail view of the enhanced ECG chart, in accordance with an embodiment of the present invention. In the example described herein, processor 40 presents chart 52 as a pseudo-three-dimensional ribbon chart, as described hereinbelow.

In an initial step 60, operator 30 attaches adhesive skin patches 46 to the skin of patient 28, and in a first collection step 61, processor 40 collects, from the surface electrodes in the adhesive skin patches, first data samples comprising electrical potentials produced by heart 26 at a sequence of sampling times. In an insertion step 62, operator 30 inserts probe 22 into a chamber of heart 26 (also referred to herein as the cardiac chamber), and in a second collection step 64, the processor collects second data samples of ancillary data with respect to heart 26 at the sampling times.

In embodiments of the present invention, the second data samples may comprise measurements received from one or more sensors mounted in the distal end of probe 22. For example as operator 30 advances probe 22 so that distal tip 56 engages endocardial tissue 70 and exerts force F on the endocardial tissue, as shown in FIG. 3, the ancillary data may comprise force measurements received from force sensor 54 that indicate force F. Additional examples of ancillary data that processor can receive from probe 22 or other elements of console 24 include, but are not limited to:

- A magnitude and phase of an impedance detected by the surface electrodes in adhesive skin patches 46.
- A position of distal tip 56. In some embodiments, position signals received from location sensor 38 can indicate a distance between distal tip 56 and endocardial tissue 70.
- A quality of contact between distal tip 56 and endocardial tissue 70, as indicated by force signals received from force sensor 54. The quality of contact may comprise a magnitude and a direction of force F.
- A measurement of ablation energy delivered by electrode 48 to endocardial tissue. Typically, the ablation energy varies during an ablation procedure.
- Starting and ending times indicating when ablation energy is delivered to the endocardial tissue.
- Irrigation parameters such as starting and ending times, indicating when probe 22 is delivering irrigation fluid to endocardial tissue 70, as well as pressures and temperatures of the irrigation fluid.
- A temperature of the endocardial tissue in contact with the distal tip.
- Force Power Time Integral (FPTI). FPTI is a scalar value that represents the force power time integral during ablation. During an ablation procedure, the FPTI value indicates a quality of an ablation lesion.

Based on the first data samples, processor 40 presents, on display 50, a trace of the electrical potentials collected at the sampling times in a first presentation step 66. In the example shown in FIG. 4, the trace comprises a first line 80 that plots potentials along a vertical axis 82 against time along a horizontal axis 84, wherein the potentials are measured as voltages V and the time is measured in seconds S. Finally, based on the second data samples, processor 40 presents a pseudo-three-dimensional characteristic that varies responsively to the ancillary data collected at each of the sampling times in a second presentation step 68, and the method ends. In some embodiments, processor 40 can save the first and the second data samples to memory 58.

In the example shown in FIG. 4, processor 40 presents a second line 86 that is that follows the contour of line 80, and presents slanted connecting lines 88 that connect the first line to the second line. Processor 40 presents the combination of lines 80, 86 and 88 as a "ribbon" having a pseudo-depth 90 along a "pseudo-depth" ancillary data axis 106.

While the example shown in FIG. 4 shows the ribbon having a uniform pseudo-depth 90, processor 40 can vary the pseudo-depth of the ribbon in order to indicate values of the ancillary data. For example, as operator 30 presses distal tip 56 against endocardial tissue 70, processor 40 can vary pseudo-depth 90 based on the force F. Additionally or alternatively processor 40 can vary the spacing between connecting lines 88 in order to indicate the values of the ancillary data. In some embodiments, processor 40 can vary the spacing between the connecting lines in order to indicate a distance between distal tip 56 and the endocardial tissue. For example, processor 40 can reduce the spacing between the connecting lines as distal tip 56 moves closer to and engages endocardial tissue 70.

Additional pseudo-3D effects, that processor 40 can use to present the ancillary data, include, but are not limited to:

- Depth shading. In the example shown in FIG. 4, processor shades some regions 92 that are bounded by the first, the second and the connected lines. In some embodiments, processor 40 can shade a given region 92 with different colors and/or patterns to indicate when ablation energy was delivered to the endocardial tissue.
- Thickness. Processor 40 can vary a vertical thickness (also referred to herein as height) 94 of line 80 by varying height 94 between line 80 and a line 96. In some embodiments, processor 40 can vary thickness 94 to indicate a pressure of irrigation fluid conveyed by probe 22 to endocardial tissue 70. Processor 40 can present the thickness as a rectangular "tube", and in some embodiments operator 30 can use input devices 59 to select and/or change which "sides" of the tube are visible to the operator.
- Vertical lines. Processor 40 can present vertical lines 98, thereby defining regions 100. In some embodiments, processor 40 can present lines 98 in different colors to indicate when distal tip 56 engages and disengages from endocardial tissue 70.
- Vertical shading. Processor 40 can shade regions 100 with different colors and/or patterns. In some embodiments, the shading can indicate a temperature of endocardial tissue 70 in contact with distal tip 56.
- Line color. Processor can change colors of lines 80, 86, 88, 96 and 98 in the ribbon based on values of the ancillary data.

As described supra, chart 52 comprises axes 82, 84 and 106. In some embodiments, operator 30 can instruct, using input device(s) 50, processor 40 to "rotate" chart 52 along one (or more) of the axes.

In some embodiments, the ancillary data collected by system 20 may have a binary state, such as a touch/no touch parameter (i.e., between the distal tip and the endocardial tissue). For ancillary data having a binary state, processor 40 can present any changes to the binary data as a change of transparency (e.g., transparent or opaque).

Chart 52 may incorporate a visual indication of an occurrence of an event, such as when ablation power is delivered to endocardial tissue 70. In the example shown in FIG. 4, processor 40 presents icons 102 and 104 to indicate an occurrence of multiple events such as:

- Acquiring mapping points.
- Starting and stopping an ablation procedure.
- Creating a site that presents parameters of lesion formation. The CARTO™ mapping system referenced above provides such a site as a VisiTag™ site.

Distal tip 56 exerting a high (i.e., excessive) force on endocardial tissue 70.

A system error.

Detecting a severe inaccuracy.

Starting and stopping pacing of heart 26.

Detecting that the patient's respiration needs training.

In some embodiments, icons 102 and 104 can indicate a corresponding number of the events transpiring at a given time. In additional embodiments, operator 30 use a given input device 59 to select one of the icons, and upon processor 40 receiving a signal from the given input device, the processor can present, on the display, more information of the events/occurrences. In the example shown in FIG. 4, icon 102 indicates an occurrence of nine events at a first given time, and icon 104 indicates an occurrence of five events at a second given time.

While embodiments herein describe processor 40 presenting chart 52 on display 50, presenting two-dimensional chart 52 with pseudo-3D characteristics on other types of two-dimensional output devices is considered to be within the spirit and scope of the present invention. For example, processor 40 can present chart 52 with pseudo-3D characteristics on a printer or as an image projected on a flat surface by a projector.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method, comprising:
   receiving first data samples of electrical potentials produced by a heart at a sequence of sampling times, wherein the first data samples are collected from body surface electrodes;
   receiving second data samples of ancillary data with respect to the heart at the sampling times, wherein the second data samples are collected by one or more sensors contained within a distal end of a flexible probe inserted into the heart; and
   generating, based on the first and second data samples, a trace of the electrical potentials collected at the sampling times, the trace having a pseudo-three-dimensional (pseudo-3D) characteristic that varies responsively to the ancillary data collected at each of the sampling times, the trace comprising a ribbon chart having a ribbon including a first line and a second line following a contour of the first line, the first and second lines defining a depth along a pseudo-depth ancillary data axis of the ribbon chart.

2. The method according to claim 1, wherein the ancillary data comprises measurements selected from a list consisting of ablation energy, a location of the distal end of the flexible probe, a measurement of a force exerted by the distal end on endocardial tissue of the heart, a quality of contact between the distal end and the endocardial tissue, a magnitude and a phase of impedance detected by the body surface electrodes, a temperature of the endocardial tissue, a Force Power Time Integral, and irrigation fluid parameters.

3. The method according to claim 1, wherein the pseudo-3D characteristic is selected from a list consisting of third lines connecting the first and the second lines, a shading of one or more regions between the first and the second lines, a thickness of the ribbon, shading the thickness of the ribbon, and a color of the ribbon.

4. The method according to claim 1, wherein the ribbon chart has multiple axes comprising a vertical axis, a horizontal axis and the pseudo-depth ancillary data axis, and further comprises rotating the ribbon chart along one of the axes.

5. The method according to claim 1, and comprising generating an icon on the ribbon chart indicating an occurrence of one or more events, and providing information on the one or more events upon receiving an input selecting the icon.

6. The method according to claim 1, and comprising saving the first and the second data samples to a memory.

7. An apparatus, comprising:
   a console having one or more processors; and
   a non-transitory computer readable medium storing a plurality of instructions, which when executed, cause the one or more processors to:
   receive first data samples of electrical potentials produced by a heart of a patient at a sequence of sampling times, wherein the first data samples are collected by a plurality of surface electrodes,
   receive second data samples of ancillary data with respect to the heart at the sampling times, wherein the second data samples are collected by one or more sensors at the distal end of a flexible probe; and
   generate, based on the first and second data samples, a trace of the electrical potentials collected at the sampling times, the trace having a pseudo-three-dimensional (3D) characteristic that varies responsively to the ancillary data collected at each of the sampling times, the trace comprising a ribbon chart having a ribbon including a first line and a second line following a contour of the first line, the first and second lines defining a depth along a pseudo-depth ancillary data axis of the ribbon chart.

8. The apparatus according to claim 7, wherein the ancillary data comprises measurements selected from a list consisting of ablation energy, a location of a distal end of the catheter, a measurement of a force exerted by the distal end on endocardial tissue of the heart, a quality of contact between the distal end and the endocardial tissue, a magnitude and a phase of impedance detected by the body surface electrodes, a temperature of the endocardial tissue, a Force Power Time Integral, and irrigation fluid parameters.

9. The apparatus according to claim 7, wherein the pseudo-3D characteristic is selected from a list consisting of third lines connecting the first and the second lines, a shading of one or more regions between the first and the second lines, varying a thickness of the ribbon, a shading of the thickness of the ribbon, and a color of the ribbon.

10. The apparatus according to claim 7, wherein the ribbon chart has multiple axes comprising a vertical axis, a horizontal axis and the pseudo-depth ancillary data axis, and wherein the instructions, when executed, further cause the one or more processors to rotate the ribbon chart along one of the axes.

11. The apparatus according to claim 7, wherein the instructions, when executed, further cause the one or more processors to generate an icon on the ribbon chart indicating an occurrence of one or more events, and to provide information on the one or more events upon receiving an input selecting the icon.

12. The apparatus according to claim 7, wherein the instructions, when executed, further cause the one or more processors to save the first and the second data samples to a memory.

13. A computer software product comprising computer-readable program code to be executed by one or more processors when retrieved from a non-transitory computer-readable medium, the program code including instructions to:
- receive first data samples of electrical potentials produced by a heart of a patient at a sequence of sampling times, wherein the first data samples are collected by the plurality of surface electrodes,
- receive second data samples of ancillary data with respect to the heart at the sampling times, wherein the second data samples are collected by the one or more sensors at the distal end of the flexible probe; and
- generate, based on the first and second data samples, a trace of the electrical potentials collected at the sampling times, the trace having a pseudo-three-dimensional (pseudo-3D) characteristic that varies responsively to the ancillary data collected at each of the sampling times, the trace comprising a ribbon chart having a ribbon including a first line and a second line following a contour of the first line, the first and second lines defining a depth along a pseudo-depth ancillary data axis of the ribbon chart.

* * * * *